United States Patent [19]
Failli et al.

[11] 4,000,284
[45] Dec. 28, 1976

[54] PHENOXYISOBUTYRIC ACID SALTS

[75] Inventors: Amedeo Failli, Montreal; William T. Robinson, Kirkland; Dushan Dvornik, Mount Royal, all of Canada

[73] Assignee: American Home Products Corporation, New York, N.Y.

[22] Filed: Sept. 8, 1975

[21] Appl. No.: 611,092

[52] U.S. Cl. .................. 424/263; 260/295.5 S; 260/295.5 R; 260/295.5 B
[51] Int. Cl.$^2$ ............. A61K 31/395; C07D 213/55
[58] Field of Search ............. 260/295.5 A, 295.5 R, 260/295.5 S, 295.5 B; 424/263

[56] References Cited
UNITED STATES PATENTS 3,717,649   2/1973   Castaigne .................. 260/295.5 R

OTHER PUBLICATIONS

Netherlands Application No. 6,500,136, dated Aug. 2, 1965, abstracted by Chem. Abstracts, vol. 64(3), 3422g–3423–e (Jan. 1966).

*Primary Examiner*—Alan L. Rotman
*Attorney, Agent, or Firm*—Stephen Venetianer

[57] ABSTRACT

Salts of phenoxyisobutyric acids with amino acid pyridylmethyl esters are disclosed. The salts possess antihyperlipoproteinemic activity. In addition, methods for their preparation and use, as well as pharmaceutical compositions thereof, are disclosed.

9 Claims, No Drawings

PHENOXYISOBUTYRIC ACID SALTS

BACKGROUND OF THE INVENTION a. Field of the Invention

This invention relates to phenoxyisobutyric acid salts having valuable pharmaceutical properties, to processes for preparing said salts, to pharmaceutical preparations thereof and to a method for using said salts.

b. Prior Art

The association of excessive plasma concentrations of lipoproteins or of plasma lipids with increased risk of heart attack, stroke, and sudden death is well established. Consequently, the consensus of informed opinion is that elevated levels of cholesterol and/or triglycerides should be reduced by appropriate long term therapy.

The generally accepted Frederickson-Levy-Lees classification of lipid disorders based on lipoprotein disturbances lists five catagories, Types I to V, of hyperlipoproteinemia. This classification allows a more rational choice of therapeutic programs for the treatment of hyperlipoproteinemia, see R. I. Levy, Fed. Proc. 30, 829 (1971). Although a variety of drugs are available for the treatment of hyperlipoproteinemia, none of them is adequate for the general treatment of all types of hyperlipoproteinemias. At the present time, the preferred drugs for treating hyperlipoproteinemia are dependent on the classification of the syndrome and are thus specific for each syndrome; for example, see R. S. Lees and D. E. Wilson, New Engl. J. Med., 284, 186 (1971). The phenoxyisobutyric acid salts of this invention have been found to be effective for reducing levels of cholesterol and triglycerides in the blood of mammals exhibiting hyperlipoproteinemia and associated conditions. The acid salts are effective at dosages which do not elicit undesirable side effects. Furthermore, the salts are effective for treating hyperlipoproteinemia in general, notably the syndromes comprising hyperlipoproteinemias of Types IIa, IIb, III and IV.

The phenoxyisobutyric acid salts are prepared by a convenient process from readily available starting materials. Consequently, the salts are inexpensive and readily available.

The phenoxyisobutyric acid salts feature a combination of chemical subunits; namely, a pyridylmethyl ester of an amino acid associated with a phenoxyisobutyric acid. Related prior art compounds include 3-pyridylmethyl esters of phenoxyalkanoic acid, U.S. Pat. No. 3,369,025, issued Feb. 13, 1968 and N-(carboxyalkyl)-phenoxyalkanoic acid amides, U.S. Pat. No. 3,364,249, issued Jan. 16, 1968. These prior art compounds are distinguished from the compounds of the present invention in that they are not salts, and moreover they lack one of the chemical subunits (i.e., an amino acid residue or a pyridylmethyloxy residue) of the compounds of this invention. Additional prior art compounds are chlorophenoxyisobutyric acid salts in which the base is a 2-aminoethanol ester or derivative thereof of nicotinic acid, see U.S. Pat. No. 3,717,649, Feb. 20, 1973, and Swiss Pat. No. 513,166, Nov. 15, 1971. The latter compounds lack the amino acid residue of the compounds of this invention.

SUMMARY OF THE INVENTION

The phenoxyisobutyric acid salts of this invention are represented by formula I,

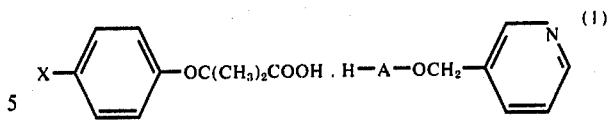

in which X is bromo, chloro or lower alkyl, and A is an amino acid residue, for example, $NHCH_2CO$, $NHCH(CH_3)CO$, $NHCH[CH_2CH(CH_3)_2]CO$, $NH[CH(CH_3)_2]CO$, $NHCH(CH_2C_6H_5)CO$ and

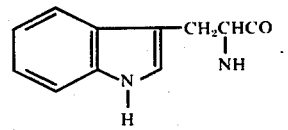

For convenience the latter radicals hereinafter represented by the symbols Gly, Ala, Leu, Val, Phe and Trp, respectively.

The compounds of formula I possess hypocholesterolemic and triglyceride lowering properties. When administered to mammals they lower concentrations of blood cholesterol and triglycerides. Accordingly, they are useful for the treatment of hyperlipoproteinemia and associated conditions.

Also included within the scope of this invention are pharmaceutical compositions comprising a compound of formula I and a pharmaceutical acceptable carrier.

The compounds are prepared readily by processes disclosed herein.

DETAILS OF THE INVENTION

The term "hyperlipoproteinemia" as used herein contemplates an increase over and above normal levels in one or more of the plasma lipoprotein classes and includes conditions wherein the concentrations in the plasma of cholesterol, triglycerides or both are increased.

The term "lower alkyl" as used herein contemplates hydrocarbon radicals having one to three carbon atoms and includes methyl, ethyl, isopropyl and propyl.

The term "amino acid" as used herein contemplates α-amino carboxylic acids and includes those isolated from natural sources upon hydrolysis of typical proteins. Furthermore, the term encompasses D, L or mixtures of D, L isomers of the amino acids and is not limited by the asymmetry of carbon atoms contained therein. Descriptions of such amino acids are found in general textbooks; for example, see K. D. Kopple, "Peptides and Amino Acids", N. A. Benjamin; Inc., New York, 1966, pp. 4 – 7.

The hypocholesterolemic and triglyceride lowering properties of the compounds of formula 1 of the present invention are demonstrated in standard pharmacologic tests, for example, in procedures similar to the in vivo tests described by C. H. Duncan and M. M. Best, Amer. J. Clin. Nutr., 10, 297 (1962), and by the general tests described by L. W. Kinsell in "Pharmacologic Techniques in Drug Evaluation", Vol. 2, P. E. Siegler and J. H. Moyer, Eds., Year Book Medical Publishers, Inc., Chicago, 1967, pp. 711 – 720.

Noteworthy is the finding that comparable lowering of serum cholesterol and of triglycerides is effected by a compound of formula 1, for example, the salt of 2-(4-chlorophenoxy)-2-methylpropionic acid with the 3- pyridylmethyl ester of glycine, at one half or less the dose required by clofibrate calculated on a molar basis. Also noteworthy, is the finding that the latter compound of formula 1 produces in rats a fall in serum triglyceride levels at a molar dose at which clofibrate, clofibric acid or glycine 3-pyridylmethyl ester have no effect.

When used as antihyperlipoproteinemic agents, a blood cholesterol and triglyceride lowering amount of the compounds of formula 1 is administered to hyperlipoproteinemic mammals, for example rats, either alone or with pharmaceutically acceptable carriers, the proportion of such carriers being determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the phenoxyisobutyric acid salts will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 50 mg per kilo per day, although as aforementioned variations will occur. However, a dosage level that is in the range of from about 1.0 mg to about 30 mg per kilo per day is most desirably employed to achieve effective results.

Process

The following is a schematic representation of the process for preparing the phenoxyisobutyric acid salts of formula 1

The step is accomplished readily by coupling the N-protected amino acid of formula 2 in the form of an activated carboxyl with 3-pyridinemethanol. Procedures used for preparing activated carboxyls are well known and descriptions of their preparation and use are found in textbooks of peptide chemistry; for example K. D. Kopple, "Peptides and Amino Acids", W. A. Benjamin, Inc., New York, 1966, pp. 45 – 51 and E. Schröder and K. Lubke, "The Peptides"; Vol. 1, Academic Press, New York, 1965, pp. 77 – 128. Examples of the activated form of the terminal carboxyl are acid chloride, anhydride, azide, activated ester, o-acyl urea of a dialkylcarbodiimide or imidazolide.

A convenient and effective method for accomplishing this coupling reaction involves reacting the appropriate N-protected acid of formula 2 with substantially an equivalent amount of 3-pyridinemethanol in the presence of substantially one equivalent of dicyclohexylcarbodiimide (DCC) in the presence of an inert organic solvent, for example, ethyl acetate, tetrahydrofuran or chloroform. Reaction times and temperatures are not critical for this reaction and can vary two or three hours to three or 4 days at 0° to 100° C. A convenient choice of time and temperature includes 24 to 72 hours at 20° to 40° C. Thereafter the precipitated urea derivative is removed from the reaction and the solvent evaporated to give the desired N-protected pyridylmethyl ester of formula 3.

With reference to R, suitable protective groups include (1) aliphatic urethan protective groups illustrated by tert-butyl-oxycarbonyl, diisopropylmethoxycarbonyl, biphenylisopropyloxycarbonyl, isopropyloxycarbonyl, tert-amyloxycarbonyl, ethoxycarbonyl, allyloxycarbonyl; (2) cycloalkyl urethan type protective groups illustrated by cyclopentyloxycarbonyl, adamantyloxycarbonyl, d-isobornyloxycarbonyl, cyclohexyloxycarbonyl; nitrophenylsulfenyl, tritylsulfenyl, $\alpha$, $\alpha$-dimethyl-3,5-dimethoxybenzyloxycarbonyl and trityl. A preferred $\alpha$-amino protective group for R is tert-butyloxycarbonyl (Boc).

In the next step, the N-protected pyridylmethyl ester 3 is deprotected under acidic conditions to give the "deprotected" pyridylmethyl ester of formula 4. Convenient conditions for this deprotection step comprise subjecting the ester of formula 3 to an excess (1.5 to 10 equivalents) of a strong acid, for example, hydrogen

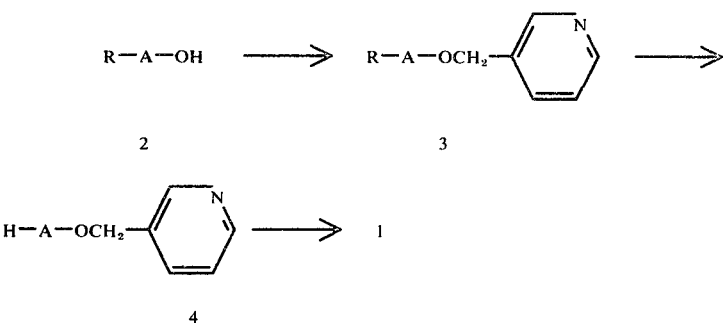

wherein R is an $\alpha$-amino protective group and A is an amino acid radical, for example, Gly, Ala, Leu, Val, Phe and Trp.

First, a N-protected amino acid of formula 2 is coupled with 3-pyridinemethanol to give the N- protected amino acid pyridylmethyl ester of formula 3. A number of methods are available for effecting this coupling.

chloride, trifluoroacetic or hydrofluoric acid, in a anhydrous inert solvent, for example, ethyl acetate, tetrahydrofuran or methylene dichloride, at −20° to 10° C for about one to 24 hours. Preferred conditions include hydrogen chloride at 0° to 10° C for 18 to 24 hours. Thereafter removal of excess acid and the solvent affords the desired "deprotected" pyridylmethyl ester of formula 4 in the form of an acid addition salt, said acid in this instance corresponding to the strong acid used for the deprotection step.

Finally, the latter compound, i.e., the acid addition salt is neutralized with a suitable base in the presence of 0.8 to 1.2 equivalents, preferably 1.0 equivalents of the appropriate phenoxyisobutyric acid of formula

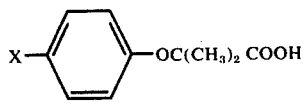

in which X is bromo, chloro or lower alkyl to give the corresponding compound of formula 1 of this invention. Convenient conditions for neutralizing the strong acid addition salt of the pyridylmethyl ester of formula 4 include dissolving the salt in an anhydrous medium, for example, anhydrous methanol, ethanol or tetrahydrofuran, and adding sufficient base, for example, potassium or sodium hydroxide, to the solution to neutralize the acid. The resulting salt containing the anion of said strong acid is then removed from the mixture by filtration, and the desired compound of formula 1 is isolated by evaporation of the filtrate.

The requisite phenoxyisobutyric acids are described in U.S. Pat. No. 3,262,850, July 26, 1966.

The following examples illustrate further this invention.

EXAMPLE 1 tert-Butyloxycarbonylglycine 3-Pyridylmethyl Ester (3; R = Boc, A = Gly)

A stirred solution of tert-butyloxycarbonylglycine (Boc-Gly-OH, 11.38 g, 65 mmole) and 3-pyridinemethanol (8.86 g, 81.25 mmole) in dry ethyl acetate (500 ml) is treated dropwise at 0° C (ice-water bath) with a solution of DCC (13.38 g, 65 mmole, redistilled) in dry ethyl acetate (250 ml).

The mixture is stirred for an additional 60 minutes at 0° C and then for 24 hr at room temperature [reaction checked by thin layer chromatography (tlc) using silica and benzene-AcOH 7:1.5 ]. **The mixture is filtered cold to remove insoluble dicyclohexylurea. The latter is washed with cold ethyl acetate and the filtrate is evaporated to dryness under reduced pressure at 20° C. The residual yellow solid is subjected to chromatography [silica (Merck), 0.05 – 0.2 mm, 100-fold, benzene-isopropanol-pyridine, 90:10:0.2]. The pure fractions are combined and evaporated to dryness. The residue is treated with ethyl acetate, filtered (to remove residual dicyclohexylurea) and the filtrate again evaporated to dryness under reduced pressure at about 20° C.

The residue is recrystallized from warm ethyl acetate/hexane to give the pure title compound, mp 82° – 83.5° C.

In the same manner but replacing Boc-Gly-OH with Boc-Phe-OH, tert-butyloxycarbonyl-L-phenylalanine 3-pyridylmethyl ester, mp 73° – 75° C, is obtained. Likewise by replacing Boc-Gly-OH with Boc-Ala-OH, Boc-Val-OH, Boc-Leu-OH or Boc-Trp-CH, tert-butyloxycarbonylalanine 3-pyridylmethyl ester, tert-butyloxycarbonylvaline 3-pyridylmethyl ester, tert-butyloxycarbonylleucine 3-pyridylmethyl ester or tert-butyloxycarbonyltryptophan 3-pyridylmethyl ester are obtained, respectively.

EXAMPLE 2

Glycine 3-Pyridylmethyl Ester Dihydrochloride

[4.2HCl; A = Gly]

A stirred and cooled (0° C) solution of tert-butyloxycarbonylglycine 3-pyridylmethyl ester (5.32 g, 20 mmole) in dry ethyl acetate (40 ml) is treated dropwise with a solution of hydrogen chloride dry ethyl acetate (3N, 33.3 ml, 100 mmole, 5 equivalents).

The mixture is stirred 18 hr at room temperature (ca. 20° – 22° C). The solvent is removed under reduced pressure at about 20° C. The residue is stirred with anhydrous ether (20 minutes) in the cold (0° – 10° C). The solid is collected, washed with ethyl acetate and anhydrous ether and dried under reduced pressure (over $P_2O_5$) to give the title compound, mp 190° – 192° C (sintering at 189° – 190° C).

In the literature the title compound is reported to have mp 195° C, see Fr. Demande No. 2,121,608, Sept. 29, 1972 [Chem. Abstr. 78, 136087b (1973)].

In the same manner but replacing tert-butyloxycarbonylglycine 3-pyridylmethyl ester with tert-butyloxycarbonyl-L-phenylalanine 3-pyridylmethyl ester, L-phenylalanine 3-pyridylmethyl ester dihydrochloride, $[\alpha]_D^{25} = + 22.4$ (c = 1, DMF), is obtained.

Likewise by replacing tert-butyloxycarbonyglycine 3-pyridylmethyl ester with tert-butyloxycarbonylalanine 3-pyridylmethyl ester, tert-butyloxycarbonylvaline 3-pyridylmethyl ester, tert-butyloxycarbonyileucine 3-pyridylmethyl ester or tert-butyloxycarbonyltryptophan 3-pyridylmethyl ester, alanine 3-pyridylmethyl ester dihydrochloride, valine 3-pyridylmethyl ester dihydrochloride, leucine 3-pyridylmethyl ester dihydrochloride and tryptophan 3-pyridylmethyl ester dihydrochloride are obtained, respectively.

EXAMPLE 3

2-(4-Chlorophenoxy)-2-Methylpropionic Acid Salt with the 3-Pyridylmethyl Ester of Glycine ( 1; X = Cl and A = Gly).

A stirred solution of glycine 3-pyridylmethyl ester dihydrochloride (4.06 g, 17 mmole) and 2-(4-chlorophenoxy)-2-methylpropionic acid (3.646 g, 17 mmole) in anhydrous methanol (100 ml) is treated dropwise at 0° C with a solution of KOH in anhydrous methanol (0.8N, 42.5 ml, 34 mmole, 2 equivalents; resulting pH ca. 6.5). Stirring is continued for one hour at 0° C. The mixture is filtered (to remove precipitated KCl) and the filtrate is evaporated to dryness under reduced pressure at 20° C. Anhydrous ether (50 ml) is added to the residue (pale yellow oil) and the resulting suspension is stirred for 15 – 20 minutes at 20° – 22° C. The colourless solid is collected, washed with dry ether and dried under reduced pressure (over $P_2O_5$) to constant weight. This crude material is repeatedly extracted (at room temperature) with anhydrous ethyl acetate (3 × 150 ml and 1 × 100 ml) to remove residual KCl. The extracts are combined and evaporated under reduced pressure at 20° C to a small volume. Anhydrous ether (120 ml) is then added. The suspension is stirred for ca. 30 minutes at 20° to 22° C. The fluffy material is collected, washed with ether and dried under reduced pressure (over $P_2O_5$) to yield the title compound.

For anaylsis a sample of the above product is dried at 50° C under reduced pressure to give the title compound; mp. 99° – 100° C (sintering at 98° C); i.r.

(CHCl$_3$) ν: ca. 2500, 1750 and 1590 cm$^{-1}$, u.v. (MeOH): 287 nm (ε=926), 280 nm (ε=1,270), 266 nm (ε=2,610), 258 nm (ε=3,130), 254 nm (ε=2,725 ), 228 nm (ε=10,460).

In the same manner but replacing gylcine 3-pyridylmethyl ester dihydrochloride with L-phenylalanine 3-pyridylmethyl ester dihydrochloride, 2-(4-chlorophenoxy)-2-methylpropionic acid salt with the 3-pyridylmethyl ester of L-phenylalanine, mp 112° C (sintering at 109° C); [α]$_D^{25}$ = + 5.9 (c = 1, DMF); i.r. (CHCl$_3$) ν 1740 cm$^{-1}$.

Likewise by replacing glycine 3-pyridylmethyl ester dihydrochloride, with alanine 3-pyridylmethyl ester dihydrochloride, valine 3-pyridylmethyl ester dihydrochloride, leucine 3-pyridylmethyl ester dihydrochloride or tryptophan 3-pyridylmethyl ester dihydrochloride, 2-(4-chlorophenoxy)-2-methylpropionic acid salts of the 3-pyridylmethyl ester of alanine, the 3-pyridylmethyl ester of valine, the 3-pyridylmethyl ester of leucine and the 3- pyridylmethyl ester of tryptophan are obtained, respectively.

In the same manner as described for the preparation of any compound of formula 1 in this Example but replacing 2-(4-chlorophenoxy)-2-methylpropionic acid with 2-(4-bromophenoxy)-2-methylpropionic acid or a 2-[4-(lower alkyl)phenoxy]-2-methylpropionic acid, the corresponding 2-(4-bromophenoxy)-2-methylpropionic acid or 2-[4-(lower alkyl)phenoxy]-2-methylpropionic acid salt with the 3-pyridylmethyl esters of glycine, alanine, valine, leucine, or tryptophan are obtained, respectively.

We claim:

1. A compound of formula 1

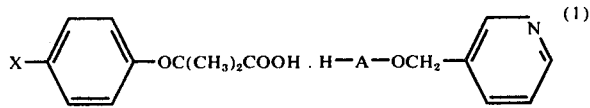

(1)

in which X is bromo, chloro or lower alkyl and A is an amino acid residue selected from the group consisting of NHCH$_2$CO, NHCH(CH$_3$)CO, NHCH[CH$_2$CH(CH$_3$)$_2$]CO, NH[CH(CH$_3$)$_2$]CO, NHCH(CH$_2$C$_6$H$_5$)CO and

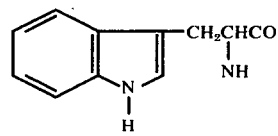

2. 2-(4-Chlorophenoxy)-2-methylpropionic acid salt with the 3-pyridylmethyl ester of glycine, as claimed in claim 1.

3. 2-(4-Chlorophenoxy)-2-methylpropionic acid salt with the 3-pyridylmethyl ester of L-phenylalanine, as claimed in claim 1.

4. A method for lowering concentrations of blood cholesterol and triglycerides in mammals which comprises administering to said mammals a blood cholesterol and triglyceride effective lowering amount of a compound of formula 1 as claimed in claim 1.

5. The method of claim 4 in which the compound of formula 1 is 2-(4-chlorophenoxy)-2-methylpropionic acid salt with the 3-pyridylmethyl ester of glycine.

6. The method of claim 4 in which the compound is 2-(4-chlorophenoxy)-2-methylpropionic acid salt with the 3-pyridylmethyl ester of L-phenylalanine.

7. A pharmaceutical composition comprising an effective lowering amount for blood cholesterol and triglycerides of a compound of formula 1 as claimed in claim 1 and a pharmaceutically acceptable carrier.

8. The pharmaceutical composition of claim 7 in which the compound of formula 1 is 2-(4-chlorophenoxy)-2-methylpropionic acid salt with the 3-pyridylmethyl ester of glycine.

9. The pharmaceutical composition of claim 7 in which the compound of formula 1 is the salt of 2-(4-chlorophenoxy)-2-methylpropionic acid with L-phenylalanine 3-pyridylmethyl ester.

* * * * *